United States Patent
Garcia Armenta

(10) Patent No.: US 11,510,903 B2
(45) Date of Patent: Nov. 29, 2022

(54) SYNERGIC PHARMACEUTICAL COMPOSITION OF THE ACTIVE ENANTIOMER (S)-KETOROLAC AND GABAPENTIN FOR THE TREATMENT OF NEUROPATHIC PAIN

(71) Applicants: Federico Amezcua Amezcua, Jalisco (MX); Carlos Amezcua Amezcua, Jalisco (MX)

(72) Inventor: Patricia del Carmen Garcia Armenta, Jalisco (MX)

(73) Assignees: Federico Amezcua Amezcua, Jalisco (MX); Carlos Amezcua Amezcua, Jalisco (MX)

( * ) Notice: Subject to any disclaimer, the term of this patent is extended or adjusted under 35 U.S.C. 154(b) by 0 days.

(21) Appl. No.: 15/734,068

(22) PCT Filed: Jun. 5, 2019

(86) PCT No.: PCT/MX2019/000064
§ 371 (c)(1),
(2) Date: Dec. 1, 2020

(87) PCT Pub. No.: WO2020/009560
PCT Pub. Date: Jan. 9, 2020

(65) Prior Publication Data
US 2021/0220330 A1    Jul. 22, 2021

(30) Foreign Application Priority Data

Jul. 4, 2018 (MX) .................... MX/a/2018/008286

(51) Int. Cl.
| | | |
|---|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/407* | (2006.01) |
| *A61P 25/02* | (2006.01) |
| *A61P 29/00* | (2006.01) |
| *A61K 9/00* | (2006.01) |
| *A61K 31/197* | (2006.01) |

(52) U.S. Cl.
CPC .......... *A61K 31/407* (2013.01); *A61K 9/0053* (2013.01); *A61K 31/197* (2013.01); *A61P 25/02* (2018.01); *A61P 29/00* (2018.01)

(58) Field of Classification Search
None
See application file for complete search history.

(56) References Cited

FOREIGN PATENT DOCUMENTS

| CA | 2296336 A1 | 8/1998 |
| EP | 2151237 A1 | 2/2010 |
| ES | 2253825 T3 | 6/2006 |
| MX | 2013005378 A | 11/2014 |
| MX | 2013005378 A1 * | 11/2014 |

OTHER PUBLICATIONS

Rasmussen et al. (Multimodal analgesia with gabapentin, ketamine and dexamethasone in combination with paracetamol and ketorolac after hip arthroplasty: a preliminary study. European journal of anaesthesiology, (Apr. 2010) vol. 27, No. 4, pp. 324-330).*
International Search Report of the ISA/ES in PCT/MX2019/000064, dated Oct. 7, 2019; 4pgs.
Narai et al., "Gabapentin Augments the Antihyperalgesic Effects of Diclofenac Sodium Through Spinal Action in a Rat Postoperative Pain Model," Anesth Analg., 115(1):189-193, Mar. 2012.

\* cited by examiner

*Primary Examiner* — Layla Soroush
(74) *Attorney, Agent, or Firm* — Haukaas Fortius PLLC; Michael Haukaas

(57) ABSTRACT

This invention refers to a pharmaceutical composition that comprises the synergic combination of a NSAID, such as the active ingredient: S-ketorolac of tromethamine and a GABA derivative agent, such as the active ingredient: gabapentin, which are formulated with pharmaceutically acceptable excipients in a single dosing unit to be administered by oral, parenteral, topical, transdermal means or with the use of transdermal, oral or nasal inhalation devices, which is indicated for the treatment of neuropathic and/or nociceptive pain caused by different etiologies.

15 Claims, 8 Drawing Sheets

SYNERGIC PHARMACEUTICAL COMPOSITION OF THE ACTIVE ENANTIOMER (S)-KETOROLAC AND GABAPENTIN FOR THE TREATMENT OF NEUROPATHIC PAIN

CROSS-REFERENCE TO RELATED APPLICATIONS

This application is a National Stage filing under 35 U.S.C. § 371 of International Application No. PCT/MX2019/000064, filed Jun. 5, 2019, which claims the benefit of Mexican Patent Application No. MX/a/2018/008286 filed Jul. 4, 2018, which applications are incorporated herein by reference.

FIELD OF INVENTION

This invention is connected with the technical field of the pharmaceutical industry, as its purpose is to provide a pharmaceutical composition that consists of the synergic drug combination of a nonsteroidal anti-inflammatory drug (NSAID), made up by the active enantiomer S-Ketorolaco or its pharmaceutically acceptable salts and an analog of gamma-aminobutyric acid (GABA) such as Gabapentin or its pharmaceutically acceptable salt, which are administered with pharmaceutically acceptable excipients or adjuvants, formulated in a single dosing unit to be administered orally. Said combination is indicated for the control and treatment of neuropathic pain.

The combination of the aforementioned active ingredients produces a stronger therapeutic effect when they are administered together in a single dosage unit than when they are administered separately, generating benefits; a smaller delivered dose, stronger therapeutic effect and fewer adverse effects.

BACKGROUND

In 2011, the International Association for the Study of Pain defined neuropathic pain as a chronic neurological complaint caused by a lesion or disease of the nervous system. Said pain is caused by a lesion or malfunction of the nervous system, damage to the nerve itself (or another part of the sensory system) and not by an abnormal activation of the pain receptors. The mechanism that generates the neuropathic pain appears in any site along the nociceptive pathways (the pathways that convey information about pain), without initially stimulating the nociceptors (pain receptors), as opposed to what happens with physiological or nociceptive pain.

Neuropathic pain is a serious syndrome with huge repercussions for the patient. One of the main causes of neuropathic pain is the most common endocrine disease: Diabetes Mellitus.

Neuropathic pain is a complex pain syndrome that groups numerous diseases, physiopathologic mechanisms, topography and clinical symptoms, being very common in clinical practice (2-40% of the population). Neuropathic pain does not stand alone as a sole symptom, since it is made up by a variety of positive sensory symptoms with different physiopathologic mechanisms that appears as pain in patients as they evoke a negative emotion. More than one symptom that caused by more than one different mechanism can coexist in the same patient, in the same way as patients that present the same symptoms respond differently to the same treatment, without us being able to predict which patients are going to respond to a particular treatment.

Neuropathic pain is caused by damage or a lesion to the central or peripheral nervous system, as spontaneous pain, manifesting in hypersensitivity to pain, with signs and symptoms that may or may not be related to the lesioned site, which makes its diagnosis and treatment hard. This pain affects millions of people around the world, although there are no precise records owing to the diversity of the associated conditions, which is why it has a highly varied etiology. Clinically speaking, it is characterized depending on its source, by a continuous or paroxysmal sharp, piercing or burning pain, with abnormal sensations of pain perception referred to as allodynia (painful response to an innocuous stimulus) and hyperalgesia (exaggerated painful response to a slightly harmful stimulus). Neuropathic pain can be produced in a variety of traumatic diseases, such as damage to the spinal cord, nerve compression and phantom leg pain member, in diseases such as diabetes, cancer, shingles, and infection with human immunodeficiency virus (HIV/AIDS), to name but a few, among other causes. Central and peripheral mechanisms are involved during the start, development and permanence of this type of pain.

A prevalence of chronic pain was found in 33.9% of adults over the age of 18, with 2.5% of the cases corresponding to neuropathic pain, in a study carried out in Manizales. Furthermore, a national study carried out between 2004 and 2005 reports a 33% frequency of neuropathic pain out of all the different types of pain, with postherpetic neuralgia being them most frequent type of pain in people over the age of 60. In 2006, Cifuentes and Lopez reported the following percentage distribution per etiology of pain for a Colombian cohort at the start of the study: radiculopathy: 43%, neuropathies: 23%, and other types of pain (multiple sclerosis, phantom leg pain, cervical lesion and pain caused by a fracture): 34%.

Whatever the etiology of the neuropathic pain, be it postherpetic, traumatic, diabetic, surgical, etc., a series of changes are produced in the afferent nociceptive pathways that include depolarization abnormalities, abnormalities in the release of neurotransmitters (both immediate and long term) and in the reorganization of the synapses in the center.

Depolarization abnormalities: When inflammatory injury is produced in the tissue that carries the nerve receptors of the pain, bradykinins, histamine, and serotonin are released. These agents have an influence on the neuronal gene transcription selecting hyperexcitable sodium channels, which causes spontaneous action potentials. Moreover, some studies suggest that, as a consequence of axonal abnormalities (traumatic, surgical, etc.), an increase is produced in the gene expression that encodes sodium channels in the nerve cell body and the motor neuron and sensory neuron dendrites, which induces hyperexcitability.

Some people propose, moreover, that the selection of a type of Na+ channels is, possibly, because the axonal ruptures produce abnormalities in the levels of neuronal growth factor circulating in the axons. All these changes contribute to lowering the pain threshold of the nociceptors and create an increase in the signal for small stimuli, a mechanism that is known as peripheral sensitization.

Abnormalities in the release of neurotransmitters: When the stimulus, produced by ectopic or high-frequency and high-intensity action potentials, reaches the dorsal horn of the spinal cord, excitatory neurotransmitters, such as substance P and glutamate. Substance P, which is released by high-frequency pulse trains, activates specific receptors NK1 and NK2 that have been connected with hyperalgesia.

Furthermore, the glutamate released by these types of anomalous potentials acts on the AMPA and kainic receptors that enable the entry of Na+. This impedes the Mg++ from blocking the NMDA Ca++ channel and thus Ca++ continuously enters in the neuron, which produces sustained depolarization and an increase in excitability. Through this mechanism, the repeated C-fiber discharges, originated by the abnormalities of the sodium channels, produce sustained depolarization or central sensitization, in such a way that the pain threshold decreases and, before small peripheral stimuli, ample central discharges are produced that are prolonged for longer than the dependent depolarizations of Na+.

But the entry of Ca++ in the neuron permits, moreover, the activation of some protein kinases dependent on Ca++, that act as second messengers (protein kinase A, protein kinase C, cyclic GMP-dependent protein kinase, nitric oxide). After activation, the protein kinases can phosphorylate several protein substrates, such as the ion channels, the membrane receptors and other enzymes that perpetuate the depolarization. Lastly, all these changes have an influence on the genetic transcription in such a way that ion channel genes with the lowest threshold are selected. All these changes have a long-term influence on patients and contribute to the pain chronification.

Neural plasticity and reorganization of the synapse: Allodynia is a complex process that simultaneously includes abnormality in the nociceptive endings and central sensitization described earlier. Moreover, for the initially painfree stimuli to be perceived as such, there need to be two additional mechanisms: a) Central reorganization of the afferent pathways, and b) Loss of the inhibitory mechanisms. Wherein the central reorganization of the afferent pathways, under normal conditions, lamella II of the posterior horn of the spinal cord receives the innervation of C fibers. However, in allodynia, the Ab fibers responsible for transmitting tactile pulses also reach this area of the spine and, accordingly, painfree stimuli can feel painful. When peripheral sensitization is produced and the high-frequency and high-intensity pulse trains reach the backbone, new connections dendritic and specific neuronal apoptosis are produced. Together with the neural reorganization of the posterior horn of the spinal cord, other changes are produced all along the nociceptive pathway that are only now starting to be understood. So when the ventrocaudal thalamus region is stimulated in patients with neuropathic pain, the sensation they perceive is pain, whereas if the same stimulation is given to patients without this type of pain, the sensation they perceive is heat. These findings suggest that there is also thalamic reorganization in neuropathic pain. Other studies demonstrate that, from the cortical perspective, changes are also produced in the connections of the nociceptive pathways. On analyzing the neuronal metabolism (PET) with imaging techniques we can appreciate that in patients with neuropathic pain, an expansion is produced of the area of cortical representation of pain, therefore, in this way, nociceptive stimuli affect broad cortical areas of integration and thus contribute to a higher alteration of the individual's affectivity. As for the loss of inhibitory mechanisms, the inhibitory synapses of the nociceptive pathway act on the spinal cord through interneurons and the top descending tracts. It has been demonstrated that the GABA levels of the inhibitory spinal interneurons drop in the peripheral lesions of C fibers.

Moreover, in allodynia, there is a reduction of serotonin and noradrenalin in the descending inhibitory neurons. Thus, there is a selection of AMPA/kainic receptors and, in consequence, the excitatory stimulus is conveyed and amplified towards superior nervous structures.

Clinical Symptoms

Irrespective of the etiology of pain, all the patients refer to the same symptoms, that should be specifically acknowledged in order to properly focus on the treatment:

1. Paresthesia and dysesthesias. These are produced by ectopic (axonal) discharges of Ab fibers that facilitate the excess entry of Na+ through the voltage-gated channels.

2. Continuous burning pain. This is produced by the three mechanisms described earlier: a) peripheral sensitization; b) ectopic pulses of C fibers as a consequence of the entry of Na+ through voltage-gated channels, and c) loss of inhibitory mechanisms with a reduction of serotonin and of GABA.

3. Paroxysmal or piercing pain. This is due to the activation of voltage-gated sodium channels in ectopic sources of C fibers.

Apart from the symptomatology directly derived from the pain, other disorders are associated that can have a decisive influence on the therapeutic attitude and its success:

1. Sleep alterations. There is no doubt that patients with chronic pain have sleep alterations. However, up until recently the repercussions of pain on the different phases of sleep had not been studied. During the slow-wave stage a mass entry of Ca++ is produced in the thalamic and cortical neurons, that are initially associated with changes in the gene expression. But recent studies have proven that the gene expression that has an influence on neural plasticity (the development of new connections) is mainly induced during wakefulness.

Moreover, a deafferentation of the nociceptive pulses is produced at the start of sleep. Sleep quality is lost in patients with chronic pain, a loss that is connected with more intense pain. For example, in people with fibromyalgia the length of time of sleep phase I is increased and the time of other sleep phases decreased.

2. Psychological disorders. It has been suggested that the pain associated with tissue or neurological damage can produce emotional changes and that psychological factors, even in the absence of physical damage, can produce chronic pain. The repetitive association of painful stimuli with innocuous stimuli causes a pain sensation in the initially painfree stimuli, probably because of cortical neural reorganization. In consequence, the proper treatment of pain requires research into the psychological alterations that may accompany it and that contribute to the overall experience of the pain sensation.

To summarize, most of the symptoms associated with neuropathic pain are explained by alterations in the transmission of the nerve impulse owing to changes in the permeability of the ion channels, the release of neurotransmitters and the central reorganization of the nerve fibers. However, it is important to point out that cortical reorganization makes similar lesions in different patients produce totally different experiences of pain, so aspects such as sleep and psychological alterations must always be borne in mind.

Owing to its etiology being so diverse and the physiopathological mechanism that underlies it, the vast majority of common painkillers do not generate an effective response to this type of pain. Therefore, the treatment of neuropathic pain constitutes a challenge for specialists nowadays. Proposals have been made based on specific evidence and recommendations for the treatment of neuropathic pain and these include topical lidocaine, anticonvulsants, tricyclic antidepressants, mixtures of serotonin-norepinephrine reuptake inhibitors, opioids and tramadol, of which, the anticonvulsants, antidepressants and opioids have been proposed as drugs of first choice for the treatment of neuropathic pain, on the basis of randomized controlled clinical trials. However, sometimes the benefits of these drugs can be limited by insufficient effectiveness and the adverse effects they produce. Therefore, there is still a considerable need to explore methods for the treatment of pain that point to the use of effective and safe painkillers (with minimum adverse effects). The foregoing having been said, associations have been proposed that contain two different painkillers or a painkiller with other classes of adjuvant drugs in an attempt to produce the maximum painkilling effect and lower the undesired effects to better treat neuropathic pain. Gabapentin is currently used in the clinical treatment of neuropathic pain; however, when the pain relief with gabapentin is not enough, the addition of a second painkilling agent, which can be an opioid or a nonsteroidal anti-inflammatory painkiller (NSAID), has been recommended.

The aims of the treatment of neuropathic pain consist of eliminating pain completely or lowering it within very short periods of time, improving the patient's functionality and quality of life.

Gabapentin is an analog of gamma-aminobutyric acid (GABA), a drug that was initially developed to facilitate the inhibitory transmission and cut down on seizure activity. Paradoxically, pharmacological studies revealed that it behaved as a powerful antiepileptic agent despite the fact that it did not have most of its expected actions on GABA, although it could increase its synthesis and release it did not combine with GABAA or GABAB receptors, it did not affect the metabolism or reuptake of the endogenous GABA and, most significantly, its actions were not blocked by selective blockers of both types of receptors. Said results seemed to prove that that the action of gabapentin on the GABAergic pathways could not be responsible for its painkilling effects. However, some studies and results nuanced this conclusion. Thus, Ng et al. have described how gabapentin is an agonist of the GABAB g b 1 a-g b 2 heterodimer that is coupled to a potassium channel subtype known as Kir 3,1/3,2. The consequence of this gabapentin action would be nerve hyperpolarization with a reduction in bioelectric activity. Another study performed on healthy volunteers has shown that gabapentin acutely and chronically increases the cerebral GABA contents, probably by means of the non-vesicular release of this neurotransmitter.

A second possibility is that gabapentin acts by impeding the activation of the glutamate receptors, especially the NMDA, through direct or indirect actions. These receptors are complex structures and can, for example, be pharmacologically actuated on the agonist binding-site (glutamate), the associated ion channels or the glycine binding-site. Gabapentin does not act on the first two, but there are some indirect studies that indicate that it could do so on the third, as its effects are reverted by the administration of D-serine, an agonist of the glycine fixation site. The expected result of such interaction would be a reduction in the activation of such receptors by glutamate. Furthermore, electrophysiology studies have shown how gabapentin can even lower the release of glutamate in the posterior horn of the spinal cord. Gu and Huang have suggested that the action of gabapentin is exercised on the NMDA receptors in a selective and dependent fashion, as gabapentin does not exercise any action on the activation of NMDA receptors under normal conditions, but this does appear when the cells have a high content of protein-kinase C (PKC). The intracellular concentration of PKC increases in response to the sustained activation of the NMDA receptors, as would happen after a nerve lesion that has clinical symptoms of hyperalgesia and allodynia.

But perhaps, the most peculiar mechanism of action of gabapentin is binding to a specific site, the a2d subunit, present in all the voltage-gated calcium channels (CCDV) that have been studied to date. The physiological role of this subunit is to increase the functional expression of the complexes of the calcium channels. At the present time three distinct subunits: a2d-1, a2d-2 and a2d-3 have been characterized, but gabapentin only binds with the first two, especially a2d-1. Thus, by fixing onto the a2d subunit, gabapentin blocks the entry of calcium through the presynaptic calcium channels, especially the P and Q, but also the L. In this way the release of neurotransmitters would be inhibited in several areas of the central nervous system. However, this action is not unanimously considered to be the one that explains the painkilling effect of gabapentin as for some authors the dose needed to block such channels is much higher than the one that is effective in a clinical setting. The answer to this contradiction might lie in the fact that gabapentin acts more effectively when there is excessive nervous activity, as in the case of epilepsy and neuropathic pain.

Gabapentin is the compound:
1-Aminomethyl-cyclononanol acid
Represented by formula (11):

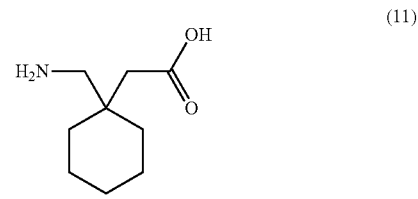 [SMILES: NCC1(CC(=O)O)CCCCC1]

(11)

Described for the first time in the U.S. Pat. No. 4,024,175 for the treatment of certain forms of epilepsy, fainting fits, hypokinesia and brain injuries. They also cause on improvement of brain functions. In consequence, they are also particularly useful for the treatment of geriatric patients.

Gabapentin exercises pharmacological actions on the different structures that participate in nociceptive transmission. the painkilling effect on neuropathic pain is probably a consequence of such multiplicity, which is necessary for it to achieve its known clinical effectiveness. Apart from its actions on the excitatory glutamate transmission and inhibitory GABA transmission, its binding to calcium channels and the activation of potassium channels may have a relevant role in the reduction of the hyperexcitability present in the clinical conditions for which it is used.

In relation to nonsteroidal anti-inflammatory drugs, the racemic ketorolac is a drug belonging to this NSAID family that is an effective painkiller in the clinical setting for the treatment of post-surgical pain.

Nonsteroidal anti-inflammatory drugs (NSAIDs) are commonly used in the treatment of acute and chronic pain and inflammation. These acidic NSAIDs act as ligands for a broad range of enzymatic and non-enzymatic proteins. Although several of these interactions can be biologically significant, in general NSAIDs exercise most of their pharmacological and toxicological effects through the specific inhibition of the binding of arachidonic acid to COX, thus avoiding the production of proinflammatory prostaglandins such as prostaglandin E2 (PGE2). Including the correlation between the inhibition of the in vitro or ex vivo synthesis of prostaglandins and the in vivo anti-inflammatory and pain-killing effects. The most significant side effects of NSAIDs are ulcerogenicity and nephrotoxicity. In general, all the NSAIDs being used at the present time inhibit both COX-1 and COX-2. However, there are signs that the anti-inflammatory activities of NSAIDs can depend on the inhibition of COX-2. One indication is the recent discovery of selective COX-2 inhibitors that exhibit anti-inflammatory activity with low ulcerogenic effect in animals. A second indication is the expression of COX-2 selectively on inflammation sites. Therefore, the inhibition of COX-2 can, in part, explain the therapeutic utility of NSAIDs, while the inhibition of COX-1 can be responsible for some side-effects, such as gastric and kidney damage.

NSAIDs, including derivative of 2-arylpropionic acid, are chiral compounds and are to be found in two enantiomeric forms. Ketoprofen, ketorolac and flurbiprofen are representative of chiral NSAIDs and are widely used in therapeutic agents as anti-inflammatory and painkilling agents such as racemates. In vitro studies have documented that the enantiomer of chiral NSAIDs can differ in their pharmacodynamic behavior, in other words, the inhibition of the synthesis of prostaglandins. It has been demonstrated that the inhibition of the cyclooxygenase by the NSAIDs is predominantly, if not exclusively, because of the enantiomer of S configuration.

The chemical structure of the racemic Ketorolac salt is as follows:

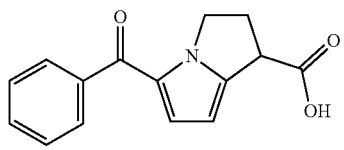 [SMILES: O=C(c1ccccc1)c1ccc2n1CCC2C(=O)O]

While the chemical structure of the new chemical compound S-(-)-Ketorolac Tromethamine is:

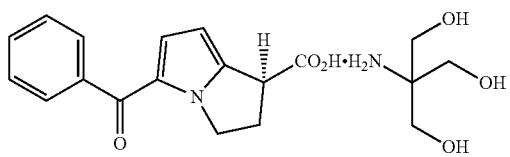

And its nomenclature is:
S-(-)-5-Benzoyl-2,3-dihydro-1H-pyrrolizine-1-carboxylic acid of 2-amino-2-(hydroxymethyl)-1,3-propanediol (1:1)
Salt of the S-(-)-benzoyl-2,3-dihydro-1H-pyrrolizine-1-carboxylic acid with 2-amino-2-(hydroxymethyl)-1,3-propanediol (1:1)

The enantioselective interaction of aryl chiral acids with prostaglandin synthase have been used to investigate catalytic mechanisms and the structure of the enzyme. The crystalline structure of X Rays has led to the identification of the active cyclooxygenase site as a hydrophobic channel, which is also the NSAID binding site. These studies supported the different ability of the enantiomers of chiral NSAIDs to inhibit the activity of the COX enzymes. A wide range of in vivo trial systems have been used to assess the anti-inflammatory, painkilling, antipyretic and toxicological properties of the enantiomeric and racemic forms. For most chiral NSAIDs, it has been demonstrated that the in vivo activity mainly lies in the S enantiomer, with a pattern of enantioselectivity and inhibition of the COX enzymes.

Preclinical studies have demonstrated the antinociceptive effectiveness of morphine and GABA, individually administered in the treatment of neuropathic pain induced by a chronic constriction of the sciatic nerve in rats (CCI), and the effect of the combination of these drugs in neuropathic pain from CCI has already been determined. Preclinical results have also been reported that establish that gabapentin in simultaneous administration with a NSAID painkiller (naproxen) can interact in an additional or synergic way in the case of thermal hyperalgesia.

Neuropathic pain is a challenge to be treated and a lot of patients have pain that is impervious to existing treatment. In randomized clinical trials (RCTs) that have examined the pharmacotherapy, no more than half the patients experience significant clinical pain relief, which is nearly always partial, not total relief. Moreover, the patients frequently experience insufferable adverse effects and are often, as a consequence, not able to tolerate the treatment. RCTs results have shown that the patients, on average, continue to have moderately serious pain despite taking drugs prescribed for their pain.

Although each painkilling agent has its advantages and disadvantages in comparison with others, there is no perfect painkiller and no painkiller that can treat all types of pain on its own. Therefore, pain therapy could, under certain conditions, be improved with the use of a combination of painkillers. A combination is more effective when the individual agents act through different pharmacological mechanisms, as well as on a variety of sites for action, acting in synergy. Owing to the activation of multiple pain inhibitory pathways, the combination of painkillers could provide better painkilling effectiveness for a wide spectrum of pain and could also lower adverse effects. In terms of safety, a lower incidence of individual adverse events can be obtained by using minimum doses of each painkiller in combination. In this regard, in clinical practice painkiller combinations have been recommended for elderly patients and patients with chronic treatments, respectively. Given the multiple mechanisms involved in the perception of pain, therapy combined with painkillers has been recommended by the World Health Organization (OMS) and is well accepted by doctors that specialize in the management of pain.

Therefore, an effective treatment is required that provides the peripheral and neuropathic painkilling effect with a smaller dose than commonly used, in a shorter time and with fewer adverse effects. Which is why this invention consists of the combination of S-Ketorolac tromethamine and gabapentin for the treatment of neuropathic pain.

Ketorolac is a nonsteroidal anti-inflammatory agent with painkilling properties and moderate anti-inflammatory and antipyretic action. The oral administration of 10 to 30 mg of ketorolac is treated as the conventional dose for pain relief. The most frequent adverse events with Ketorolac are directly connected with the effects on the gastric tract and kidney or liver function. It inhibits platelet aggregation and can cause the formation of gastric ulcers.

Currently available scientific evidence shows that the risk of developing serious peptic ulcer complications (in particular, upper digestive hemorrhage) is consistently higher with the use of ketorolac than with other nonsteroidal anti-inflammatory drugs and that the increased risk can be especially important when it is used outside of the currently authorized conditions of use.

The S (-) enantiomer is the most active. The S enantiomer of the racemate has been determined as the one that basically has the painkilling activity, with it being almost twice the racemic form and about 60 times more potent, which makes it possible to lower the dose by up to 50% and thus reduce the risk of severe side-effects from the chronic consumption of the drugs based on the current racemic salt of Ketorolac.

Among the GABA-derivative drugs, gabapentin is a drug originally designed for use in the treatment of the epilepsy. Gabapentin is currently widely used to relief pain, especially neuropathic pain. Gabapentin is well tolerated by most patients, has a relatively mild side-effect profile and passes through the body without being metabolized.

The bioavailability of gabapentin is not proportional to the dose: as the dose increases, bioavailability decreases. With the 900 mg/day dose distributed in 3 administrations, the bioavailability reached 60%, dropping by up to 27% with the 4,800 mg/day dose. The administration of gabapentin with food slightly increases its absorption. Gabapentin binds very little with the proteins of the plasma (3%) with its apparent volume of distribution after an intravenous dose of 150 mg of 58±6 L. In patients with epilepsy, the concentrations of the drug in the cephalospinal liquid are approximately 20% of the concentrations in the plasma. Gabapentin is not appreciably metabolized and is eliminated by renal excretion. The half-life for elimination is 5 to 7 hours and is not affected when multiple doses are administered. Both plasma clearance and renal clearance are proportional to the creatinine clearance. The elimination of gabapentin is less in patients with renal dysfunction and the elderly.

Gabapentin is eliminated in hemodialysis, which is why the doses need to be readjusted for these patients and patients with kidney failure.

This invention is characterized by providing a composition that comprises the combination of an NSAID and a GABA derivative, to be more specific, the combination of S-Ketorolac tromethamine with Gabapentin. A combination capable of treating neuropathic pain.

In the state of the art, U.S. Pat. No. 6,569,463 describes solid pharmaceutical compositions for the enhanced administration of a wide variety of active pharmaceutical ingredients contained in the same or separately administered, where said pharmaceutical compositions include a solid vehicle and this contains a substrate and an encapsulation coating where said coating can include different combinations of active ingredients, hydrophile surfactants, lipophilic surfactant and triglycerides, where the active ingredients are selected from gabapentin, ketorolac, among other compounds that have intrinsic aqueous solubility of under approximately 1 mg/mL; U.S. Pat. No. 6,720,001 describes pharmaceutical emulsions of oil in water for the administration of polyfunctional active ingredients selected from gabapentin, ketorolac, among other compounds. Emulsions include an aqueous phase, an emulsifying agent and an oleaginous phase, where the oleaginous phase includes a structured triglyceride that is substantially free from triglycerides that have three residues of C6-C12 fatty acid, or a combination of a long-chain triglyceride and a polarity modifier that boosts polarity; U.S. Pat. No. 6,923,988 describes solid vehicles for a better administration of pharmaceutical compositions that comprise gabapentin, ketorolac, among other compounds, an invention that is connected with U.S. Pat. Nos. 6,720,001; 7,070,765 describes the supply of drug esters using aerosols by means of inhalation, where the method consists of a) heating a coating of a drug ester, on a solid support, to form a vapor; and, b) passing air through the heated vapor to produce aerosol particles having less than 10% drug ester degradation product in weight and MMAD of less than 5 micrometers, moreover a kit for delivering a drug ester through an inhalation route is provided that comprises: a) a thin coating of a drug ester composition and b) a device for dispensing said thin coating as a condensation aerosol; U.S. Pat. No. 7,815,936 describes a pharmaceutical composition that comprises pyrogenically produced granular silicon dioxide, that has voids, and at least one active pharmaceutical ingredient selected from gabapentin, ketorolac, among other compounds, where the granular silicon dioxide has mesopores and macropores, un medium particle diameter of 10 to 120 μm and a BET with an area of 40 to 400 $m^2/g$, determination according to DIN 66 131 using nitrogen, where the mesopores represent from 10 to 80% of the total volume and the particle size distribution of the granular material is 80% vol. higher than 8 μm and 80% lower than 96 μm and the ratio of pores lower than 5 μm is, as a maximum, 5% referred to the total volume of pore and, furthermore, the pharmaceutical composition comprises an auxiliary pharmaceutical substance; U.S. Pat. No. 8,377,994 describes a pharmaceutical composition that comprises an active pharmaceutical ingredient selected from gabapentin, ketorolac, among other compounds and similar intermediates, said composition is prepared using the pyrogenically produced silicon dioxide deaeration or decompression process: compressing the pyrogenically produced silicon dioxide by roller compaction to form intermediates with a compacted density of 185 to 700 g/L; breaking the intermediates; opcionalmente classify o sieving los intermediate; and combining them with the active pharmaceutical ingredient.

This invention is characterized by providing a composition that comprises the combination of gabapentin with S-Ketorolac tromethamine not reported in the state of the art. The potential advantage in the use of the therapy of said combination is that the painkilling effects can be maximized, while the incidence of adverse effects is minimized.

The use of this combination of drugs offers a painkilling synergy that permits a reduction in the necessary doses together with a reduction in the adverse effects.

OBJECT OF THE INVENTION

To offer a new therapeutic option for the control and treatment of neuropathic pain, that manages to reduce the patients' symptomatology and improve their quality of life. This is done by means of the strategy of reassessing a racemic drug such as ketorolac (NSAID) and separating out the beneficial part, which is the S enantiomer, to obtain a unique and pure isomer compound with a better therapeutic index than the mixture formulated as a racemate. The utility of the combination of gabapentin with the active enantiomer, S-Ketorolac tromethamine, generates synergic interaction, increasing its therapeutic potency, start of action and reduction of adverse events.

The combination of said active ingredients gives the result of greater pharmacological potency where, when based on S-Ketorolac tromethamine, it is 3.3 times more potent than Rac Ketorolac, and 1037 times more potent than AA, and that in combination with gabapentin improves the therapy, offering benefits such as: administration of smaller concentrations of the active ingredients than when administered separately, better effectiveness and greater therapeutic potency, apart from significantly lowering the probability of side effects that can arise when they are administered independently in comparison to when they are administer separately.

DETAILED DESCRIPTION OF THE INVENTION

Figure 1:
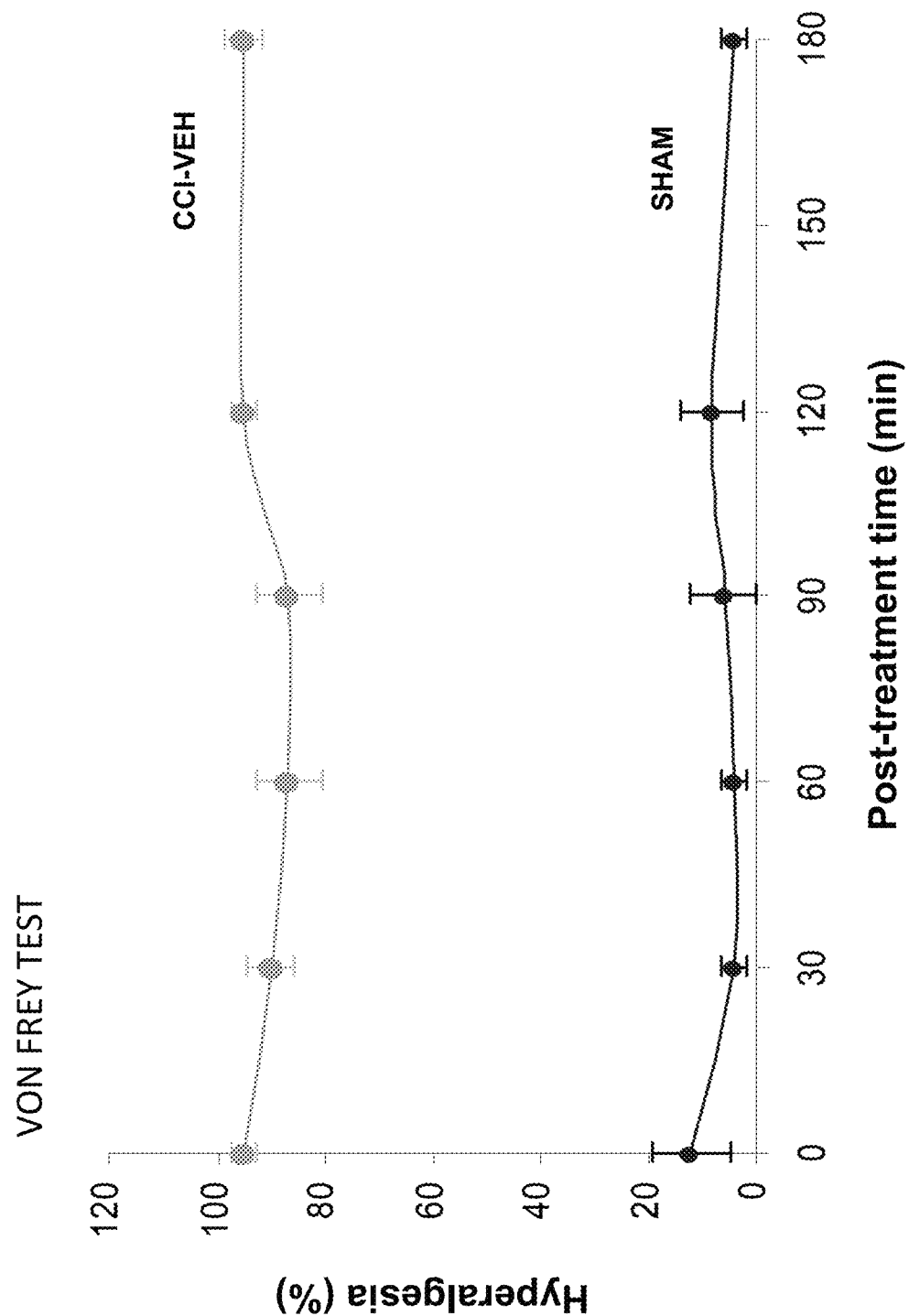
FIG. 1. Von Frey test for CCI-VEH and SHAM.

The management of neuropathic pain is known to be complex and the response to existing treatments is insufficient, even with drugs that have been established on the basis of consensual recommendations, effectiveness is unpredictable, the dosage can be complicated and adverse effects are common. This invention has demonstrated with preclinical tests that the novel combination of gabapentin with S-Ketorolac tromethamine in particular dosages shows an unexpected and strong therapeutic synergic effect in the treatment of neuropathic pain; for which reason the main purpose of this invention is to develop a pharmaceutical composition made up the combination of an analog anticonvulsant agent of the gamma-aminobutyric acid (GABA) neurotransmitter such as gabapentin and the active non-steroidal anti-inflammatory (NSAID) enantiomer S-(−)-Ketorolac Tromethamine of the family of frequent use as painkiller, antipyretic and anti-inflammatory. Said combination is to be found formulated with pharmaceutically acceptable excipients, which is indicated for the control and treatment of neuropathic pain.

S-Ketorolac tromethamine is a painkiller that exercises its action through the inhibition of cyclooxygenase enzymes, impeding the synthesis of prostaglandins. This salt is made up by the S (−) enantiomer that is the most active, being 75 times more active than the R (−) form. which makes it possible to lower the dose by up to 50% and thus lower the severe side effects that result from the chronic consumption of the drugs based on the current racemic salt of Ketorolac, which produces an effective synergic effect, with better tolerance and fewer side-effects, using weaker concentrations of the aforementioned active ingredients, in comparison to the doses that are commonly used when said active ingredients are administered separately.

Many nonsteroidal anti-inflammatory drugs (NSAID) are marketed as racemates, compounds of a 50:50 mixture of two enantiomers. Which are non-superimposable mirror images and designated R and S. Although they are identical in respect of the physical and chemical properties, they often exhibit notable pharmacological and toxicological differences. These differences are enantioselective. The enantiomer can also suffer inversion, the conformational change of one enantiomer into another.

One currently available alternative for increasing the effectiveness of a painkilling treatment and significantly lowering the side effects is through the administration in combination of two or more active agents, such as the synergic drug combination whose protection is being sought in this invention.

This invention seeks to provide a new therapeutic option for the control and treatment of neuropathic pain, that manages to reduce the patients' symptomatology and improve their quality of life. The combination of said active ingredients gives the result of more pharmacological potency where, when based on S-Ketorolac tromethamine, it is 3.3 times more potent than Rac Ketorolac, and 1037 times more potent than AA.

The effects that the combination of gabapentin and an active painkilling enantiomer such as S-Ketorolac or its tromethamine salt can produce on neuropathic pain resulting from Institutional Customers have not been determined to date. For which, the determination and assessment were performed in this paper for the antinociceptive (anti-allodynic and anti-hyperalgesic) effect of the individual and combined administration of gabapentin and S-Ketorolac in order to determine its individual effects and the type of synergic interaction to be found for these drugs in a model for neuropathic pain induced by chronic constriction of the sciatic nerve in rats, employing allodynia and hyperalgesia tests, as well as determining possible adverse effects that said association of drugs could have, such as constipation, effects on motor coordination and modification of lethal doses and therapeutic indices and margins of safety in the model for neuropathic pain for chronic constriction in rats.

Said combination improves the therapy, offering benefits such as: administration of weaker concentrations of the active ingredients that, when they are administered separately, higher effectiveness and greater therapeutic potency, apart from significantly lowering the probability of side effects that can arise when they are administered independently in comparison to when they are administer separately.

With this invention there is a reduction in the side-effects that the separate administration of each compound could cause, through lower doses from the ones employed commercially. Therefore, the behavior of gabapentin in combination with S-Ketorolac tromethamine was preclinically demonstrated, managing to determine the interaction and synergy between both of them together with the optimal combination proportions and a high degree of therapeutic effectiveness and enhancement.

As a result of the above, the assessment was carried out of the antinociceptive effect of the acute and chronic individual and combined administration of the active enantiomer, S-(−) Ketorolac and gabapentin, to determine the type of synergic interaction that these drugs demonstrate in a model for neuropathic pain induced by chronic constriction of the sciatic nerve in rats, through (cold) allodynia and hyperalgesia tests (von Frey filaments) as well as the determination of possible adverse effects that said interaction could incur, such as the effects of fatality and the effect on motor coordination in this model for neuropathic pain in rats.

Experimental Model

Analysis of the Effectiveness (Anti-Hyperalgesia and Anti-Allodynia) on Neuropathic Pain, Synergy and Some Adverse Effects Generated by the S-Ketorolac+Gabapentin Association Administered Orally.

As for the experimental model, the model of Bennett and Xie, is one of the most widely used models for the study of neuropathic pain and its treatment, because it shows many of the physiopathologic properties of neuropathic pain in humans. Said experimental model is based on the unilateral ligature of the sciatic nerve, which produces a chronic constriction injury, (CCI). This experimental model has shown itself to be sensitive to a number of drugs that are used clinically for the symptomatic treatment of neuropathic pain. The experimental model has also demonstrated a high degree of similarity with other neuropathic pain models in terms of the degree of allodynia and hyperalgesia when faced by mechanical or thermal stimuli on time-courses, these parameters have been widely used in pharmacology and assessment of neuropathic pain Once the neuropathic pain model (8 days after the surgery) has been established, the behavior of the animals is assessed to ensure the degree of harm produced. The following observed behaviors are indicative of neuropathic pain: (1) autotomy, the animal injures itself in the denervated leg, (2) allodynia, withdrawal of the leg in the face of harmless stimulus that may be mechanical or cold (acetone), (3) hyperalgesia, violent withdrawal of the leg in the face of a moderate thermal or mechanical stimulus (Von Frey filaments 15 g). These aforementioned parameters have been widely used on pharmacology and the modulation of neuropathic pain. The tests that are most used to determine allodynia and hyperalgesia are: mechanical hyperalgesia with the von Frey filaments, the cold allodynia with acetone, thermal hyperalgesia with the plantar test and mechanical hyperalgesia with the pinprick test.

Materials and Methods:

Animals for Experimentation

Male Wistar rats [Crl:(WI)fBR], with a body weight of 120-140 g at the start of the experimental phase, which weighed 160-180 g when the drugs were administered, were used for the particular study in this invention. The animals were kept in polycarbonate boxes under conditions of controlled temperature and light, with 12-hour cycles of light/dark and ad limitum water and food intake. All the experiments were carried out during the light phase. The animals were used and managed following the guidelines established in the Ethical Guidelines for Pain Research of the International Association for the Study of Pain, and following a protocol approved by the Local Committee of Ethics for the Management of Laboratory Animals. The number of experimental animals was kept to a minimum (n=6 to 8), and, at the end of the experimental determinations, the animals were sacrificed using carbon dioxide.

Application of the Methods

The model for ICC neuropathic pain described by Bennett and Xie in 1988 was standardized. The rats were anesthetized and the sciatic nerve of the rear right leg was immediately dissected, by means of an incision, dissecting the biceps femoris to locate the part that is most proximal to the trifurcation of the sciatic nerve and apply four loose ligatures with silk thread. At the end of the surgery, the muscle was sutured with absorbable thread and the skin with silk thread. The surgery of the rats falsely operated on (Sham) was done in the same way, however, the sciatic nerve was not tied. This entire procedure was performed under aseptic conditions.

The degree of hyperalgesia and allodynia in the rats submitted to the sciatic nerve surgery was determined by means of the Von Frey test and the acetone test. These determinations were made a day before the surgery and, 7 days after the surgery a time-course of 180 minutes was done for both the control (saline) and for the compounds that were administered orally, in the study, both singly and combined, to evidence the hyperalgesia and allodynia that were present. Then a time-course was made of hyperalgesia and allodynia, but now in rats with chronic treatment (1 administration/12 hours), carrying out the determinations of both hyperalgesia and allodynia 30 minutes after the morning administration of the treatments being studied and in the following period: 0, 1, 3, 5 and 7 days (14 administrations in total).

Von Frey Test (Mechanical Hyperalgesia).

The rats were placed on a metal screen in a box of transparent acrylic where they remained for at least 10 minutes to adapt before the test. The response was determined to a tactile stimulus applied to the plantar surface of the rear right leg using the 15 g von Frey filament. The stimulus was applied 10 times at intervals of approximately 3 seconds and the percentage of response (% response=number of responses/10×100) obtained. With the 15 gram von Frey filament, the controls (sham and without surgery) showed a certain nociceptive response, so in this case the response is considered to be hyperalgesic.

Acetone Test (Cold Allodynia)

At the end of the Von Frey test, the rats were left to rest on the metal screen and after a 5-10 min period, approximately 0.1 mL of acetone was applied to the plantar surface of the rear legs using a syringe with a flexible plastic tip, below the metal grating. The time (seconds) the animal remained with its leg removed from the surface was recorded with a chronometer for 60 s after exposure to the acetone. The response time of the rear right leg was measured and three replications were made at intervals of at least 2 minutes. Once the experimental methodologies to be employed had been standardized, the researchers proceeded to the experimental design of the groups and experiments that were to be carried out.

A) Different groups of animals with neuropathic pain (ligature of the sciatic nerve) were established with each group consisting of 6 animals. The effects of mechanical hyperalgesia (15 g von Frey filaments) and cold allodynia (acetone test) were assessed in these animals, both as a reflection of the degree of neuropathic pain affecting the animals, before and after the acute and chronic treatment.

B) A control group of ICC animals that were pending for 31 days was established in order to observe the time-course of the development of hyperalgesia and allodynia, to determine the permanence over time of the hyperalgesia and allodynia.

C) A control group called SHAM was established that has only dissection without the surgery or ligature of the sciatic nerve being done. To demonstrate that neuropathic pain is only present if the proper ligature is done on the sciatic nerve.

D) A control group called CCI-VEH was established, that does have the surgery or ligature of the sciatic nerve but no pharmacological treatment.

FIG. 1 gives the results of the effects found in control groups, where the hyperalgesia response is evident (nearly 100% response in the rats that have surgery (CCI-VEH) and the lack of an anti-hyperalgesic effect of the vehicle is made evident. While the rats that were not tied (SHAM) show a small nociceptive response to being stimulated with the 15 g filament, the response is very close to zero, but they do show a certain degree of response, which proves that there is already pain or nociception with the 15-gram von Frey filament and that after the ICC surgery the rats show hyperalgesia. Said graph gives the mean±standard error.

Active Agents Used for the Design of Experiments

The ranges of useful doses of the drugs in the laboratory animals were determined in order to analyze and determine the preclinical useful doses. For the purpose of finding the range for the effective dose or to form the dose/response curve for desired effects and toxic effects, in order to then design the combinations to be analyzed.

To determine the dose/response curve (CDR) for the individual drugs (gabapentin and S-Ketorolac), individual doses of both gabapentin of 3.2, 10, 31.6, 100 and 177.8 mg/kg and S-Ketorolac 0.0316, 0.1, 0.316, 1.0, 3.16, 31.6 and 100 mg/kg were administered orally, then the antinociceptive effect was assessed using the allodynia and hyperalgesia tests, at 30, 60, 90, 120 and 180 minutes post-administration to obtain the time-course (CT) for the administration of each of the doses of those drugs.

Hyperalgesic Effects

Figure 2:
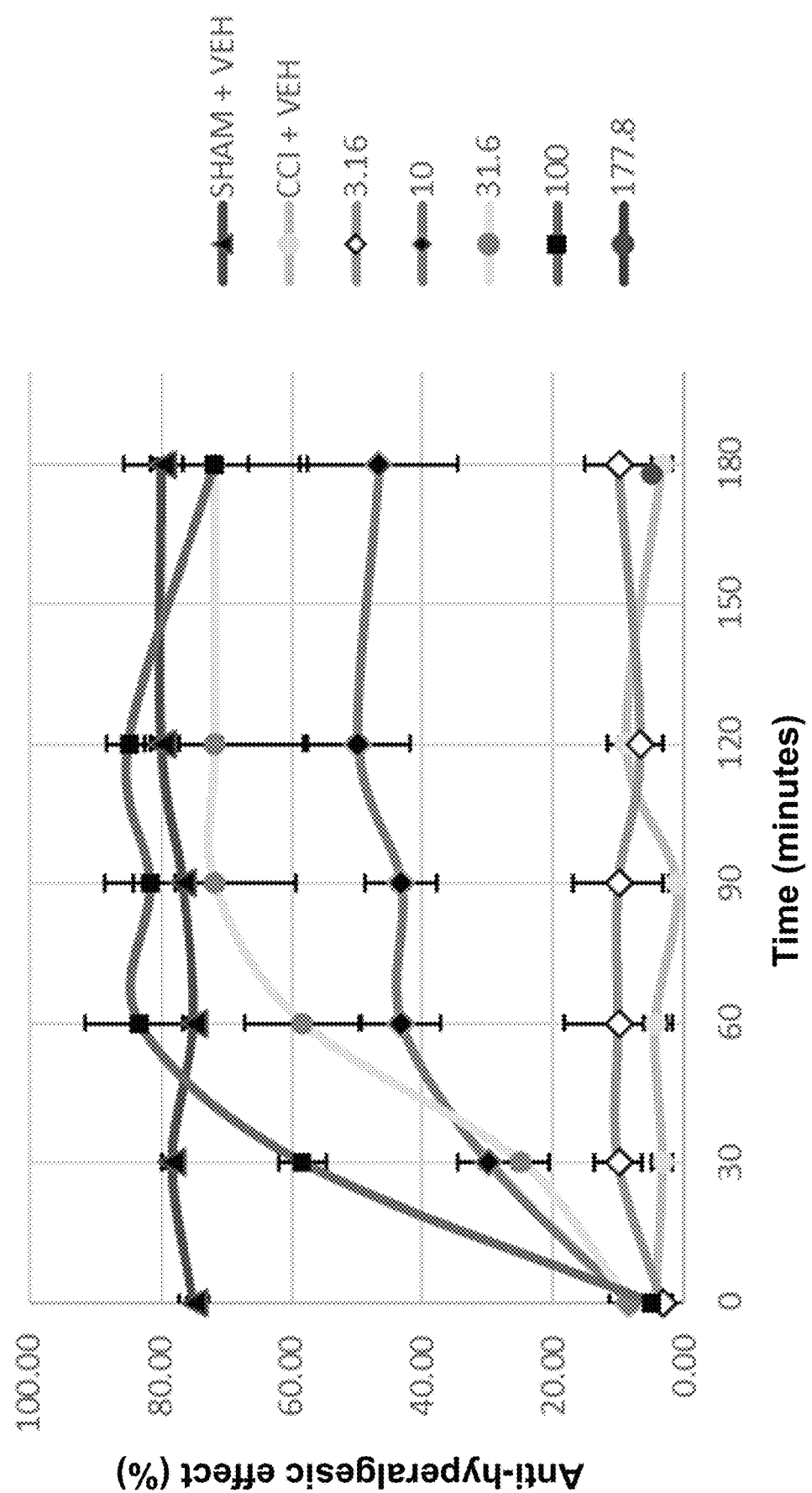
FIG. 2. Time-courses of the anti-hyperalgesic effect of Gbp with the Von Frey test in rats with a chronic constriction injury.

The response of the CTs generated by gabapentin was obtained for the hyperalgesic effects. The percentage of anti-hyperalgesic response generated by the different doses administered is assessed. Axis X shows the time in minutes with determinations at times of 0, 30, 60, 90, 120 and 180 minutes after the oral administration of each dose. Axis Y shows that at the start the animals had complete hyperalgesia and after the administration of different doses of gabapentin, relief from the hyperalgesia gradually appeared, dependent on the dose, in other words, anti-hyperalgesic effects. The mean and standard error for 6 animals is plotted at every point of the experiment, shown in FIG. 2.

Figure 3:
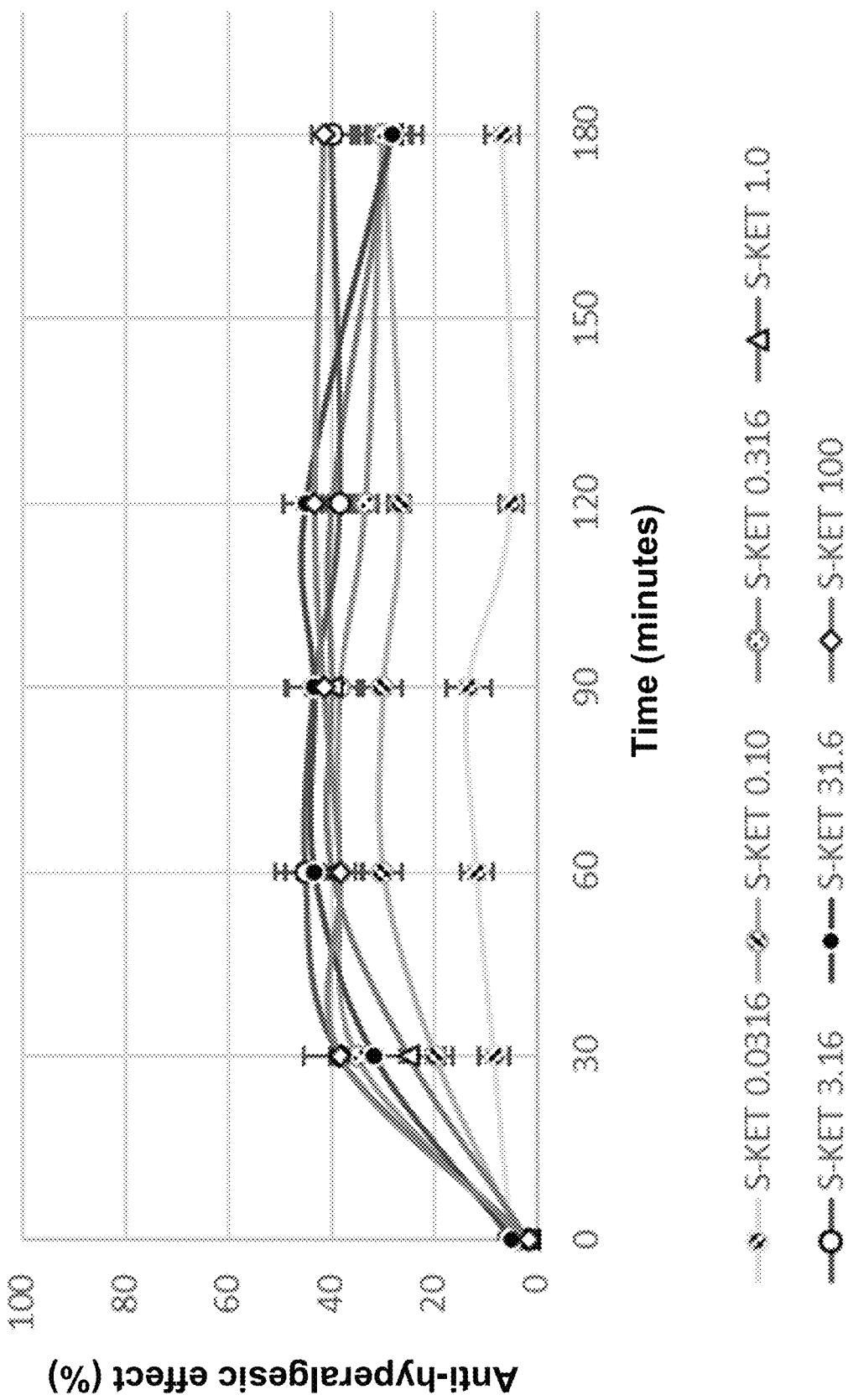
FIG. 3. Time-courses of the anti-hyperalgesic effect of S-Ketorolac (S-Ket) with the Von Frey test in rats with a chronic constriction injury.

Furthermore, the results were obtained for the response of the time-courses generated by the S-Ketorolac as can be observed in FIG. 3, that shows the anti-hyperalgesic effects generated by each of the doses of S-Ketorolac, evaluated in the animals with neuropathic pain. The percentage of anti-hyperalgesic response generated by the different doses was determined. Axis X shows the time in minutes with determinations at times of 0, 30, 60, 90, 120 and 180 minutes after the oral administration of each dose. Axis Y shows the degree of anti-hyperalgesic effect in the animals that had complete hyperalgesia at the start. After the administration of the dose of S-Ketorolac, relief from the hyperalgesia gradually appeared, dependent on the dose. The mean and standard error for 6 animals is plotted at every point of the experiment. An anti-hyperalgesic effect generated by S-Ketorolac was observed as the dose being administered increased, but only up to the dose of 3.16 mg/kg, as after that, although the dose was increased, there was no longer an increase in anti-hyperalgesic effects.

Now that the pharmacological anti-hyperalgesic characteristics of the 2 compounds in individual administration on neuropathic pain are known, the researchers proceeded to carry out the study and analysis of the interaction and type of synergy of anti-hyperalgesic effects for the simultaneous administration of these 2 drugs using the "Synergic Interaction. Surface" (SIS) method. The decision was made to assess 15 different combinations and thus be able to determine the optimal combinations both in terms of effectiveness and for the degree of anti-hyperalgesic enhancement. 3 doses from the dose/response curve for gabapentin (3.16, 10.0 and 31.6 mg/g) were taken as a basis and were combined with 5 set doses of S-Ketorolac (0.0316, 0.10, 0.31. 3.16 and 31.62 mg/kg orally). The combination of said active ingredients, 0.316 mg/kg of S-Ketorolac with 31.6 mg/kg of gabapentin, showed the strongest anti-hyperalgesic effects (the most effective combination), The anti-hyperalgesic effect produced by the compounds was observed, both alone and in combined form, and the combination(s) that generate the best or strongest effects were detected, but we cannot yet determine whether that result is a product of additive or supra-additive interaction.

Figure 4:
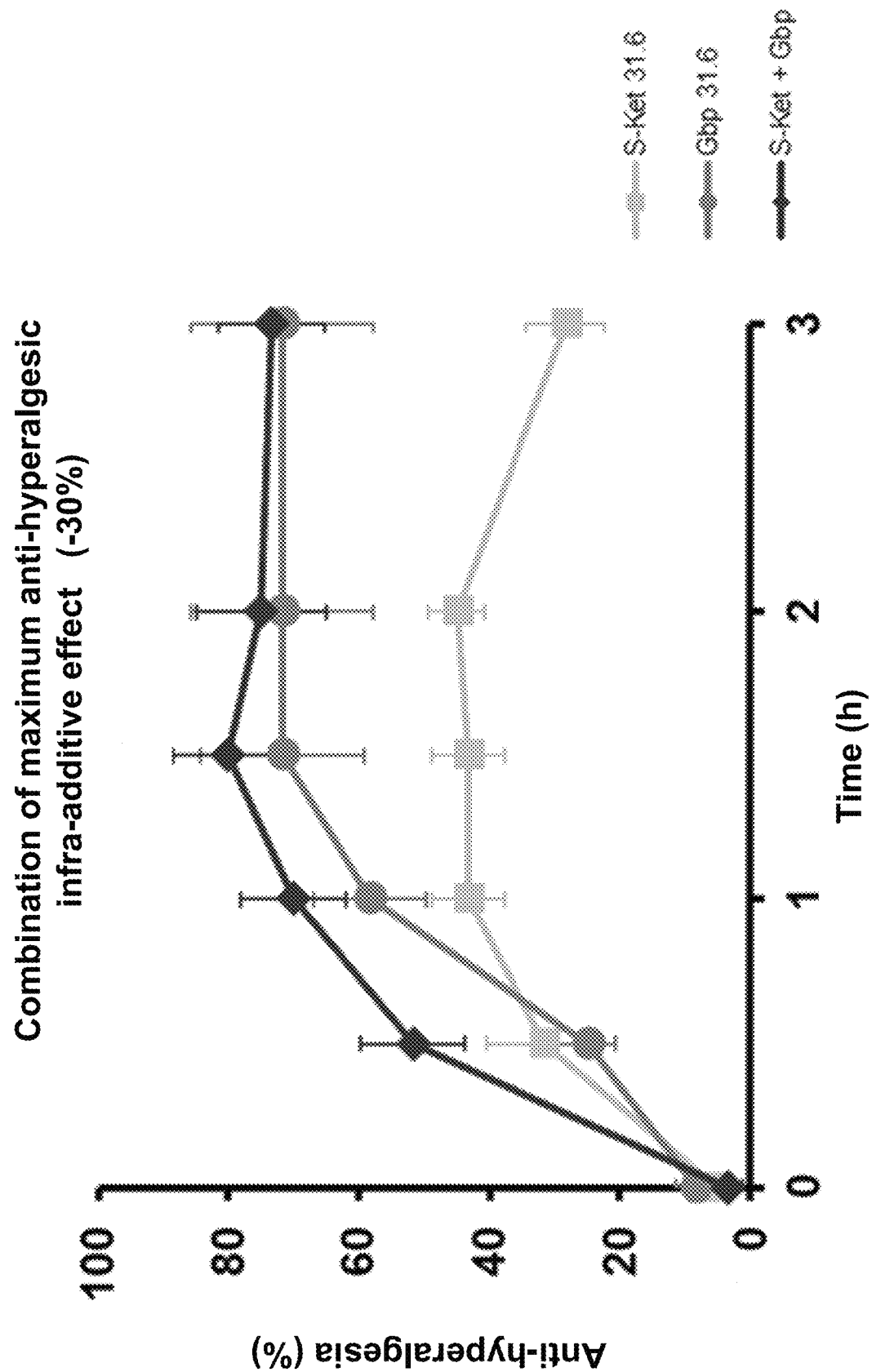
FIG. 4. Time-courses of S-Ket (31.6 mg/kg), Gbp (31.6 mg/kg), and the combination (S-Ket 31.6 mg/Kg+Gbp 31.6 mg/Kg).

From the results for combinations analyzed for anti-hyperalgesic effects, not only the ones that produced infraadditive effects are of interest but also the ones that produce anti-hyperalgesic effectiveness and the ones that produce supradditive effects. FIG. 4 shows the time-courses for the combination that showed the highest anti-hyperalgesic infraadditive effect (−30%) and the individual TC for the drugs that make up said combination. The mean and standard error are plotted. In the time-course for this infraadditive combination (31.6 mg/kg S-Ketorolac+31.6 mg/kg gabapentin) it can be observed that the maximal response (80.00±8.56%) for anti-hyperalgesic effects reached 1.5 h after administration, and the effect falls slightly until it reaches hours after the administration. When only 31.6 mg/kg S-Ketorolac, one of the components of this combination, was administered, a lower maximal response of 43.33±5.58% was reached at 1 h after administration, an effect that held for 1 more h and then fell. While 31.6 mg/kg gabapentin, the other component of this combination, only generated its maximal response (71.67±12.50%) 1.5 h after administration, and this effect held until the end of observation, 3 h after administration.

Anti-Allodynic Effects

Figure 5:
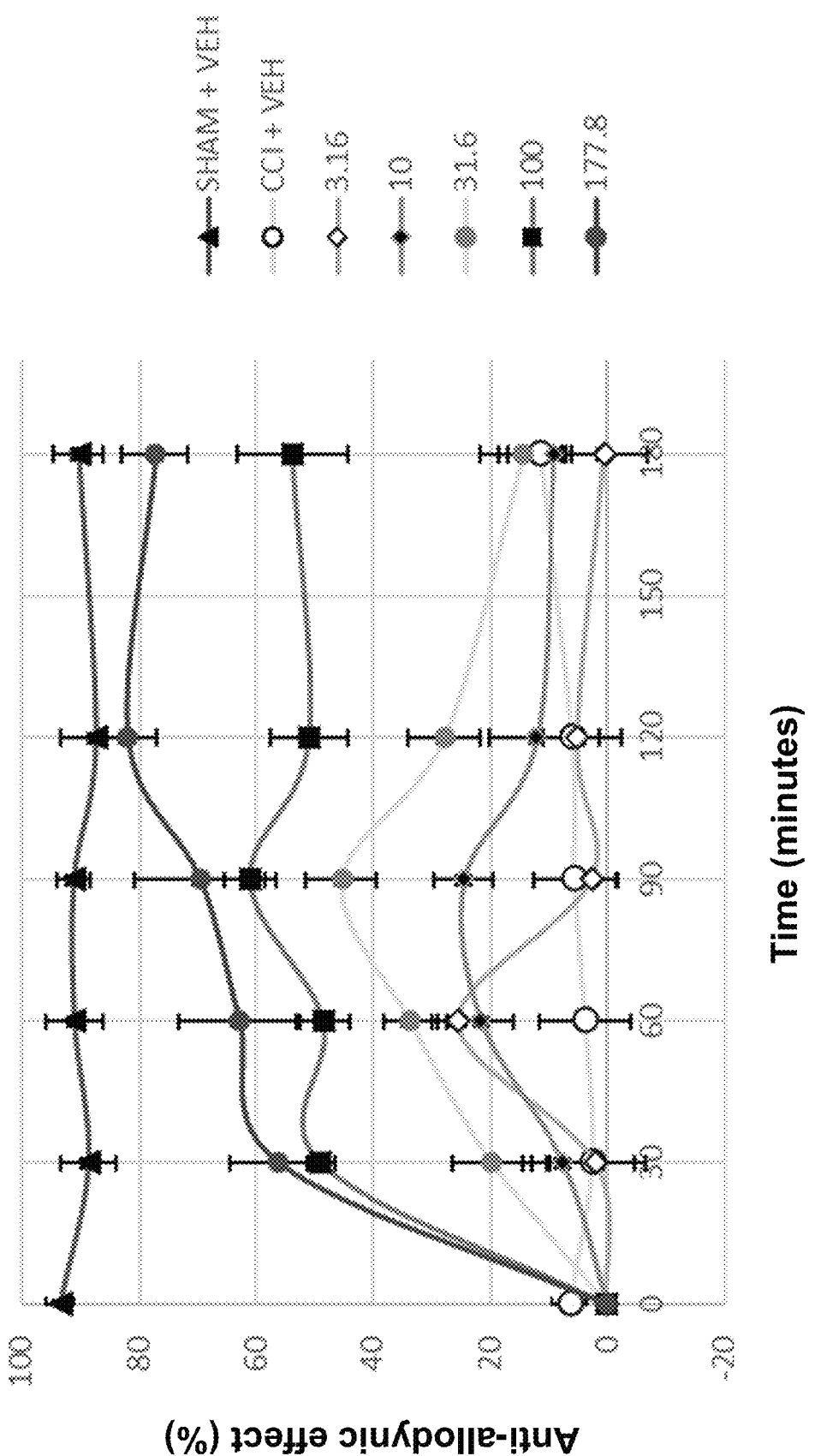
FIG. 5. Time-courses of the anti-allodynic effect of gabapentin (Gbp) with the cold allodynia test (with acetone) in rats with a chronic constriction injury.

Moreover, results were obtained that show the TC for the anti-allodynic effects generated by each of the doses of gabapentin, assessed in rats with neuropathic pain. The percentage of response anti-allodynic generated by the different doses is assessed. Axis X shows the time in minutes with determinations at times of 0, 30, 60, 90, 120 and 180 minutes after the oral administration of each dose. Axis Y shows that at the start the animals had complete allodynia, and after the administration of the dose of gabapentin gradual relief from the allodynia began to appear, dependent on the dose, in other words, anti-allodynic effects. The mean and standard error for 6 animals is plotted at every point of the experiment. There is an evident anti-allodynic effect generated by gabapentin as the dose increases. It can also be observed that while the 3.16 mg/kg dose of gabapentin practically does not generate anti-allodynic effects, the 177.8 mg/kg dose produces the maximum anti-allodynic effect, in accordance with FIG. 5.

Figure 6:
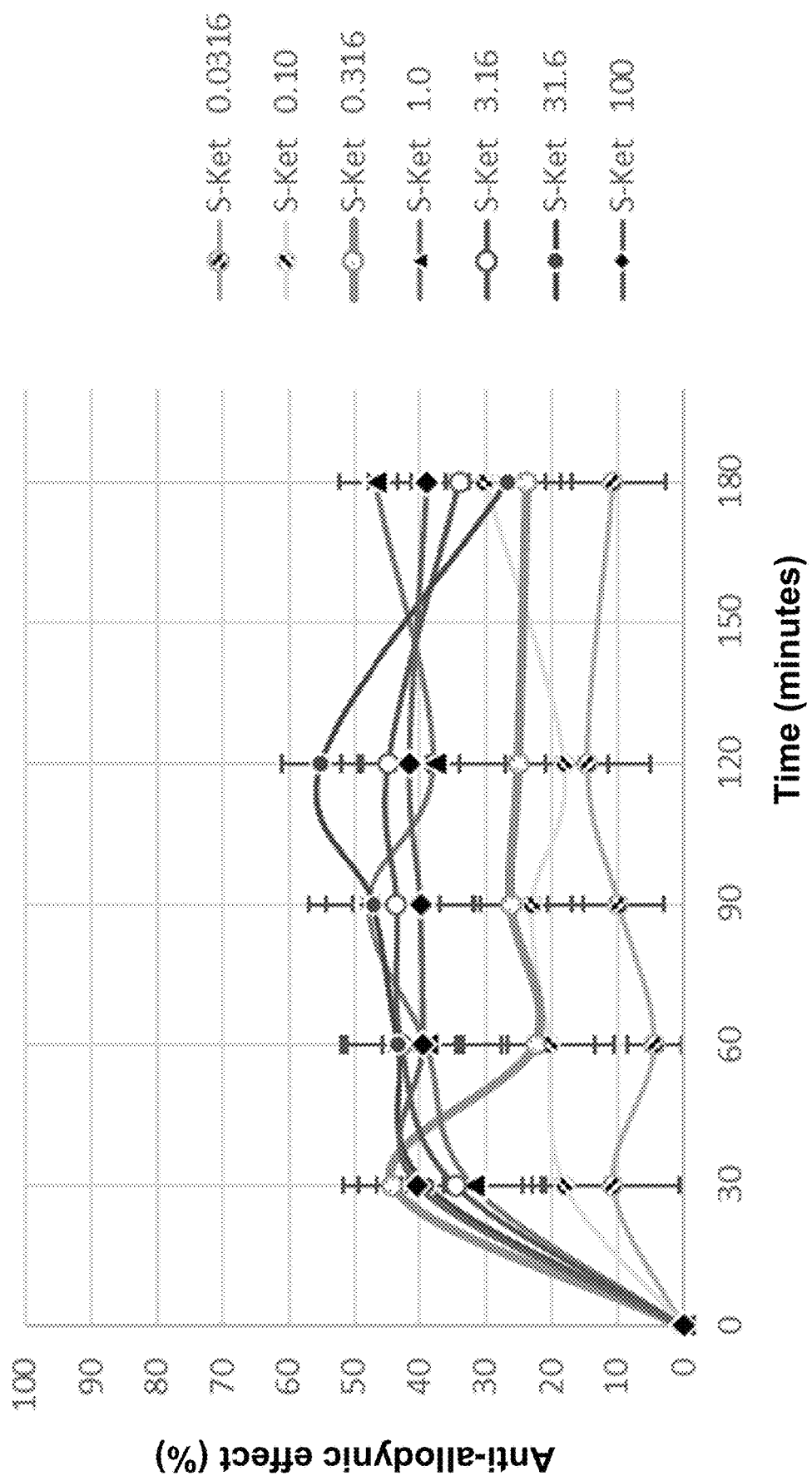
FIG. 6. Time-courses of anti-allodynic effect of S-Ketorolac (S-Ket) with the cold allodynia test (with acetone) on rats with a chronic constriction injury.

As for S-Ketorolac, results were obtained in respect of the time-courses of the anti-allodynic effects generated by each of the doses of S-Ketorolac evaluated in the animals with neuropathic pain. Axis X shows the time in minutes with determinations at times of 0, 30, 60, 90, 120 and 180 minutes after the oral administration of each dose. Axis Y shows the degree of anti-allodynic effect in the animals that had complete allodynia at the start. After the administration of the dose of S-Ketorolac, relief from the allodynia gradually appeared, dependent on the dose. The mean and standard error for 6 animals is plotted at every point of the experiment. There is an evident anti-allodynic effect generated by S-Ketorolac as the dose increases. It can be observed that while the 0.0316 mg/kg dose of S-Ketorolac generates almost no anti-allodynic effects, the 1.0 mg/kg dose already produces the maximum anti-allodynic effect, graphically demonstrated in FIG. 6.

For this invention, the design was carried out of all the combinations that were to be assessed. The decision was made to assess 15 different combination proportions in order to have a very complete idea of the type of interaction between these 2 painkillers and be able to obtain and determine the optimal combinations both in terms of effectiveness and for the degree of anti-allodynic enhancement. Given that gabapentin produced the best anti-allodynic effectiveness, and that it is the compound with "less serious" adverse effects than the adverse effects that S-Ketorolac could produce, the decision was made to take 3 doses of the CDR of gabapentin (3.16, 10.0 and 31.6 mg/kg) as a basis and combine them with set doses of S-Ketorolac, with 5 different doses of S-Ketorolac (0.0316, 0.10, 0.31, 3.16 and 31.62 mg/kg orally) being chosen.

Figure 7:
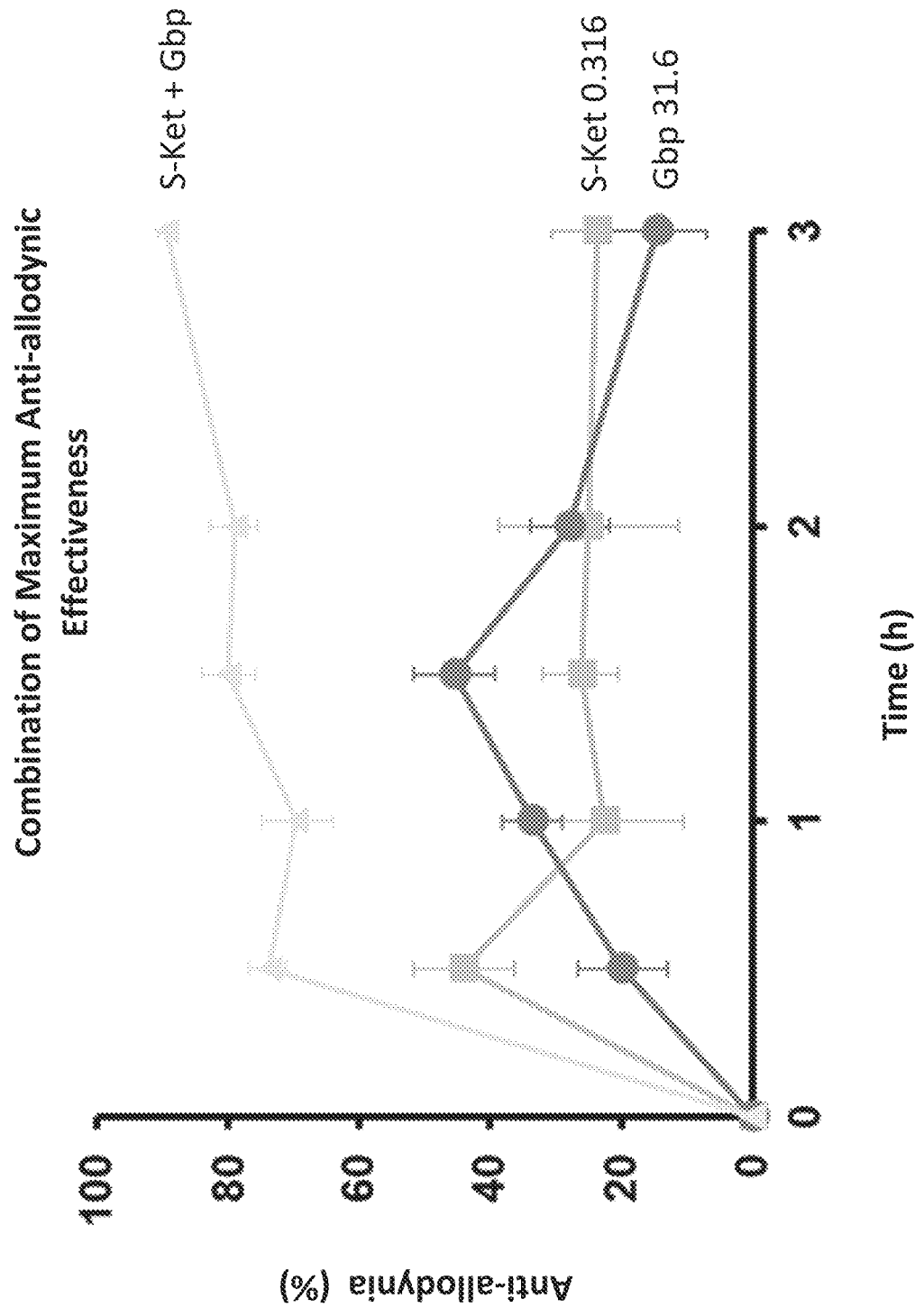
FIG. 7. Time-courses (TC) of the combination that demonstrated the highest anti-allodynic effect.

From the results of the combinations analyzed, the ones that are optimal because they produce high anti-allodynic effectiveness and a high degree of enhancement are of interest. One of the significant combinations is the one that produces the most effective anti-allodynic effect out of all the combinations. FIG. 7 gives the TC for the combination that demonstrated the highest anti-allodynic effect and that, in the respective CDR, showed itself to be the most effective combination in regards to antinociceptive anti-allodynic effects. The individual TCs of the drugs that make up said combination are also shown. The mean and standard error are plotted. It is possible to observe in the TC for the optimal combination for effectiveness (0.316 mg/kg S-Ketorolac+ 31.6 mg/kg gabapentin) that a good anti-allodynic effect of 74.00±2.85% is quickly achieved (30 minutes after administration), but the effect continues to increase until 3 hours after administration at 89.48±1.28% of anti-allodynic effect. When only 0.316 mg/kg S-Ketorolac, one of the components of the effective combination, was administered, a less maximal response was achieved of 44.00±7.71% at 30 minutes after administration and this effect dropped considerably, thus reaching the end of the assessment. Whereas 31.6 mg/kg gabapentin, the other component of the effective combination, generated its maximal response (45.40±6.20%) only after 1.5 h of administration, and afterwards the effect decreased until it reached 23.70±6.90% of anti-allodynic effect at 3 h after administration.

From the above results, the time-courses were analyzed, where gabapentin by itself is defined as producing its maximal response up to 1.5 h after its administration. But when the active ingredient, S-Ketorolac, is added to gabapentin, the result is that the new maximal response is now bigger and appears in a shorter time (less latency time) after administration: 0.5 h. In other words, with the optimal combination for effectiveness: 1) the latency at maximal response improves (decreases, which is favorable), 2) the maximal response improves (increases, which entails better relief), and 3) the anti-allodynic coverage increases (which is very useful as, at the end of the assessment when the compounds individually administered no longer has an anti-allodynic effect, the combination continues to generate and show a very adequate and high anti-allodynic effect).

As further support for this invention, the therapeutic index study was also performed on rats 24 h post-treatment, which is defined as the quotient of DL50 (24 h)/DE50. From said analysis and calculation, we get that the higher the result, the safer the drug, as this indicates the number of times it is necessary to increase DE50 for it to be turned into DL50 in the population being analyzed.

In the case of S-Ketorolac (24 h): The therapeutic index=18,541

In the case of S-Ketorolac+gabapentin (24 h): The therapeutic index=813,043

Figure 8:
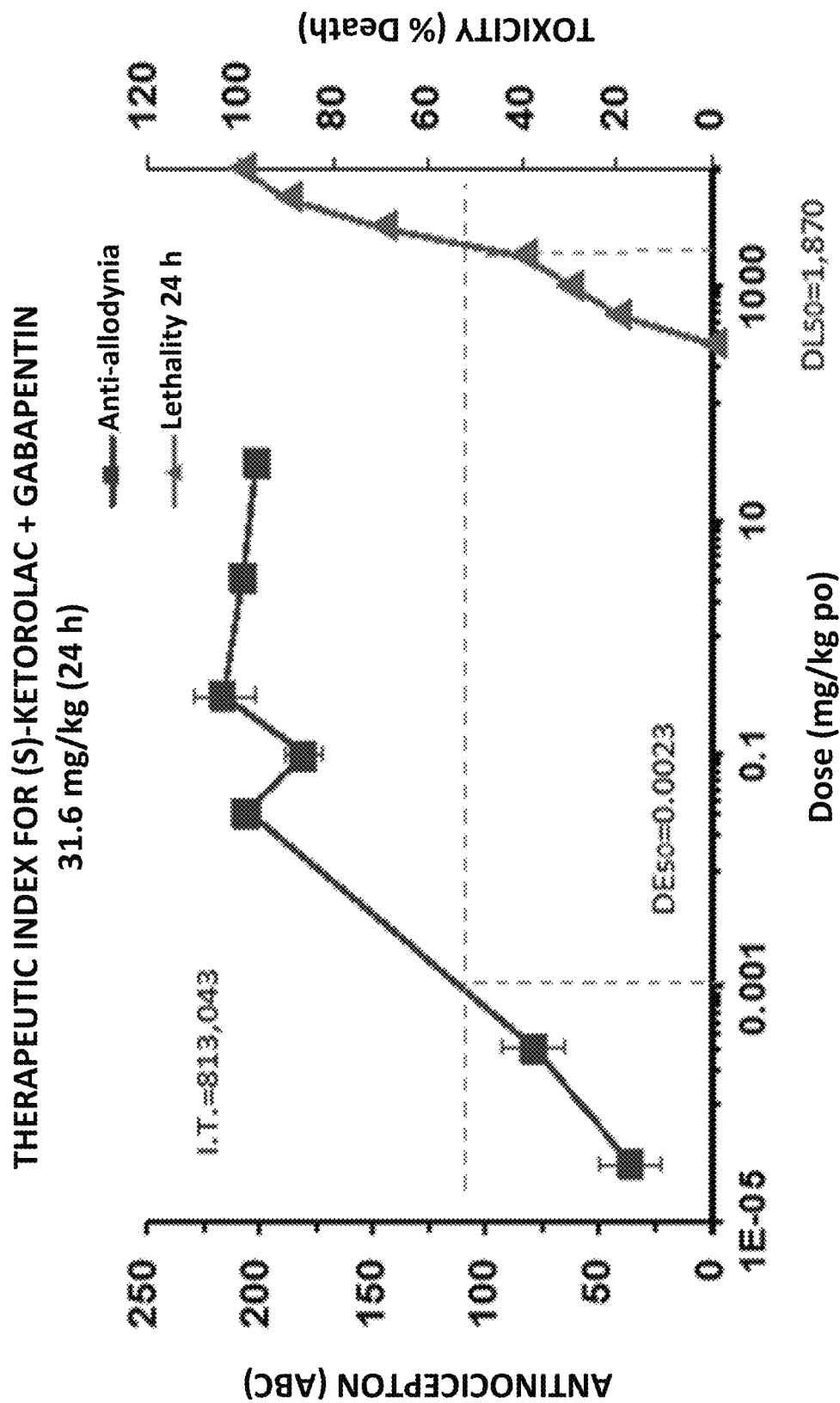
FIG. 8. CDR of desired effects (anti-allodynia) and toxic effects (death) at 72 h post-treatment with S-Ketorolac (0.316 mg/kg)+gabapentin (31.6 mg/kg). The arrow indicates the safety margin of the combination at 72 h.

That is to say that S-Ketorolac, on its own, had a very suitable therapeutic index, but now the highest therapeutic index pertains to the combination of S-Ketorolac+gabapentin. In other words, in a combination of said active ingredients, the CDR (for desired effects and lethal effects) was farther apart, therefore S-Ketorolac is safer in combination, as these variables are much farther apart. This is displayed in a graph in FIG. 8. There is less distance between the CDR (desired effects and lethal effects) of the compound alone, than between the CDR (desired effects and toxic effects) of S-Ketorolac in combination with gabapentin.

In the current state of the art, there are pharmacological treatments for pain, however, there is no one treatment that is characterized by the combination of the active agents, gabapentin and S-Ketorolac tromethamine, which is why the development of this invention provides a current safe alternative for the control and treatment of neuropathic pain, managing to lower treatment times, therapeutic effects and secondary reactions. The administration of said compounds, for each one S-Ketorolac tromethamine is given in an amount of approximately 0.01 mg to approximately 100 mg a day of treatment, while gabapentin is given in an amount of approximately 0.01 mg to approximately 1000 mg a day.

This invention is developed for oral, nasal, intramuscular, intravenous, and topical administration; either in the form of fast release for both drugs or modified release for one or both drugs, with a smaller dose, there is greater therapeutic potency and a lower risk of adverse events.

EXAMPLES

By way of illustration and not as a limitation, a description is given below of some pharmaceutical compositions:

Example 1: Compositions for Oral, Nasal and/or Topical Administration

S-Ketorolac tromethamine
Gabapentin
Pharmaceutically acceptable excipient and/or vehicle Example 2: Composition for Intramuscular and Intravenous Administration S-Ketorolac tromethamine
Gabapentin
Pharmaceutically acceptable excipient and/or vehicle This invention can be represented in other specific forms without losing its spirit or essential characteristics. The modes described shall, in all their aspects, be treated only as examples and not as restrictions. Therefore, the scope of this invention is given in the attached claims rather than in the above description. Its scope shall include all the changes that fall within the meaning and range of equivalence of the claims. As a whole, this invention provides the following advantages:

1. The combination of S-Ketorolac tromethamine with gabapentin is useful for the management of neuropathic pain.

2. Very good anti-allodynic enhancement results can be obtained with the combination of S-Ketoreolaco with gabapentin.

3. In general, better anti-allodynic than anti-hyperalgesic results can be obtained. However, making a proper selection of dose to be combined can get excellent anti-allodynic and anti-hyperalgesic effects and, moreover, using optimal combinations, the necessary doses (in combination) to produce high effectiveness against neuropathic pain can be significantly reduced with the certainty of lowering or at least not increasing adverse effects.

4. There were very big, significant and favorable changes of magnitude in the Therapeutic Indices for the combinations, in the 3 assessment times, for example: a) At 24 h the therapeutic index changed by a magnitude of 44 times, with the therapeutic index for the combination being more favorable. b) At 48 h the therapeutic index changed by a magnitude of 63 times, with the therapeutic index for the combination for the combination being more favorable, and c) at 72 h the therapeutic index changed by a magnitude of 56 times, with the therapeutic index for the combination being more favorable.

These favorable changes in the therapeutic index for the combinations in relation to S-Ketorolac by itself were also seen in the safety margin, where there were huge, significant and favorable changes for the combinations, in the 3 assessment times: a) At 24 h the safety margin changed by a magnitude of 38 times, with the safety margin for the combination being more favorable. b) at 48 h the safety margin changed by a magnitude of 104 times, with the biggest and most favorable change being in the safety margin for the combination, and c) at 72 h the safety margin changed by a magnitude of 43 times, with the safety margin for the combination being more favorable.

The invention claimed is:

1. A synergic pharmaceutical composition consisting of: 0.01 mg to 100 mg
S-Ketorolac tromethamine,
gabapentin or a pharmaceutically acceptable salt thereof, and
a pharmaceutically acceptable vehicle and/or excipient, formulated in a single dosing unit for treatment of neuropathic and/or nociceptive pain disease in mammals, wherein the S-Ketorolac tromethamine is present in the composition in an amount of 100 times less to an amount of 1000 times less than an amount of the gabapentin or a pharmaceutically acceptable salt thereof.

2. The composition of claim 1, wherein the amount of gabapentin is 300 mg per dosing unit.

3. The composition of claim 1, wherein the dosing unit comprises a capsule, a tablet, granules, a caplet, a suspension, or a solution.

4. The composition of claim 1, wherein the dosing unit comprises a sublingual tablet.

5. The composition of claim 1, wherein the composition is used to treat moderate pain.

6. The composition of any one of claim 1, wherein the mammal is a human.

7. A method for treatment of neuropathic and/or nociceptive pain disease in a mammal in need thereof, consisting of an orally administrable pharmaceutical composition consisting of:
a synergistic combination of: 0.01 mg to 100 mg
S-ketorolac tromethamine; and,
gabapentin or a pharmaceutically acceptable salt thereof; and,
a pharmaceutically acceptable vehicle and/or excipient, formulated in a single dosing unit,
wherein the S-ketorolac tromethamine is present in the composition in an amount of 100 times less to an amount of 1000 times less than an amount of the gabapentin or pharmaceutically acceptable salt thereof, wherein the composition treats neuropathic and/or nociceptive pain disease in a mammal.

8. The method of claim 7, wherein the amount of the S-ketorolac tromethamine is 5 mg per dosing unit.

9. The method of claim 7, wherein the amount of gabapentin is 150 mg per dosing unit.

10. The method of claim 7, wherein the amount of gabapentin is 300 mg per dosing unit.

11. The method of claim 7, wherein the amount of gabapentin is 400 mg per dosing unit.

12. The method of claim 7, wherein the dosing unit comprises a capsule, a tablet, granules, a caplet, a suspension, or a solution.

13. The method of claim 7, wherein the dosing unit comprises a sublingual tablet.

14. The method of claim 7, wherein the composition is used to treat moderate pain.

15. The method of claim 7, wherein the mammal is a human.

* * * * *